United States Patent [19]

Chen

[11] Patent Number: 5,380,629
[45] Date of Patent: Jan. 10, 1995

[54] METHOD OF MAKING AND A PHOTOGRAPHIC ELEMENT CONTAINING BLEACH ACCELERATOR SILVER SALTS

[75] Inventor: Benjamin T. Chen, Penfield, N.Y.

[73] Assignee: Eastman Kodak Company, Rochester, N.Y.

[21] Appl. No.: 40,318

[22] Filed: Mar. 30, 1993

[51] Int. Cl.⁶ .................... G03C 5/00; G03C 5/44; G03C 5/42; G03C 1/005
[52] U.S. Cl. ........................ 430/461; 434/30; 434/430; 434/564; 204/59 QM; 204/92; 204/157.49; 204/157.76; 549/64; 549/225; 556/113
[58] Field of Search ............ 204/59 QM, 92, 157.49, 204/157.76; 430/30, 430, 461, 564; 544/64, 225; 556/113

[56] References Cited

U.S. PATENT DOCUMENTS

| | | | |
|---|---|---|---|
| 3,821,002 | 6/1974 | Culbane et al. | 430/30 |
| 3,893,858 | 7/1975 | Wabnitz, Jr. | 96/60 |
| 3,964,983 | 6/1976 | Eisenbach et al. | 204/59 QM |
| 4,013,470 | 3/1977 | Landen, Jr. | 430/564 |
| 4,157,289 | 6/1979 | Ikenoue et al. | 430/564 |
| 4,163,669 | 8/1979 | Kanada et al. | 96/74 |
| 4,193,804 | 3/1980 | Ikenoue et al. | 430/30 |
| 4,865,956 | 9/1989 | Harder et al. | 430/430 |
| 4,923,784 | 5/1990 | Harder et al. | 430/430 |
| 5,166,015 | 11/1992 | Ichikawa et al. | 430/30 |

FOREIGN PATENT DOCUMENTS 0407206  7/1990  European Pat. Off. .
55-64237  6/1978  Japan .

*Primary Examiner*—Charles L. Bowers, Jr.
*Assistant Examiner*—J. Pasterczyk
*Attorney, Agent, or Firm*—Sarah Meeks Roberts

[57] ABSTRACT

This invention provides a process for preparing a bleach accelerator silver salt dispersion by precipitating a salt of a bleach accelerating compound and a silver salt wherein the vAg is maintained at a predetermined level during the precipitation. This invention further provides a photographic element containing a dispersion of grains of a bleach accelerator silver salt wherein the grains are isomorphic or derived from needle or platelet isomorphic crystals.

23 Claims, 1 Drawing Sheet

10 μm

10 μm
*FIG. IA*
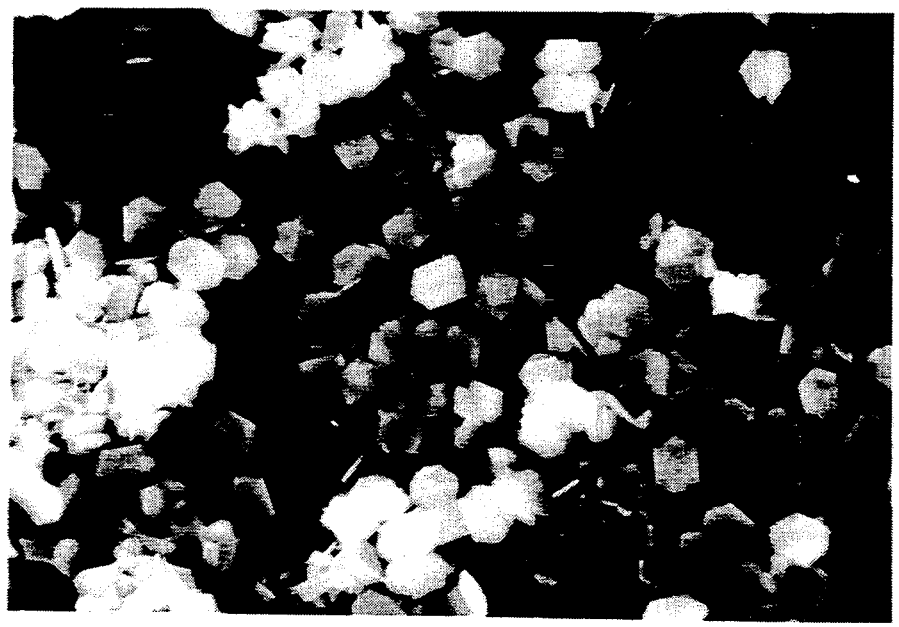
10 μm
*FIG. IB*

METHOD OF MAKING AND A PHOTOGRAPHIC ELEMENT CONTAINING BLEACH ACCELERATOR SILVER SALTS

FIELD OF THE INVENTION

This invention relates to processes for forming dispersions of bleach accelerator silver salts useful in accelerating the bleaching of developed silver halide color photographic elements. It further relates to photographic elements containing such bleach accelerator silver salts.

BACKGROUND OF THE INVENTION

A color image is formed in a color photographic element by generation of an imagewise distribution of the dye as a function of silver halide development. It is common practice to remove the silver image formed on development and the silver halide remaining in unexposed areas of the element. This is accomplished by a bleaching step in which the silver image is oxidized by a suitable oxidizing agent, commonly referred to as a bleaching agent, followed by dissolving the silver halide in a silver halide solvent, commonly referred to as a fixing agent. Alternatively, the bleaching agent and the fixing agent can be combined in a bleach-fixing solution and the silver removed in one step by the use of such a solution.

Various compounds known as bleach accelerators are often used to accelerate the bleaching process. One class of compounds, substituted thiols, have been found to accelerate bleaching either when directly added to the bleaching solution or, if introduced via a prebath, before the bleaching step. See, for example, U.S. Pat. No. 3,893,858.

U.S. Pat. No. 4,163,669 suggests that there is an advantage to incorporating a bleach accelerator directly in a photographic film but that incorporation of a free thiol would have adverse effects on the photographic properties of the film. U.S. Pat. No. 4,163,669 suggests incorporating in a photographic element certain bleach accelerators as salts of a heavy metal ion. Among the bleach accelerators mentioned are the organic thiols of the type described in U.S. Pat. No. 3,893,858.

In order to obtain bleach accelerator silver salt dispersions which can be readily incorporated into a silver-halide photographic film and which remains in stable suspension during storage, the particle size of the bleach accelerator silver salt crystals should be relatively small, for example, less than 3 microns. This small particle size has heretofore been obtained by catastrophically precipitating the bleach accelerator silver salt crystals and then incorporating them into photographic elements by a variety of techniques. Especially preferred techniques include homogenizing or ball milling a slurry of the compound in the presence of a surfactant to form finely divided particles, as disclosed in Swank et al U.S. Pat. No. 4,006,025; milling a mixture of molten compound and a molten or liquid dispersing agent, as described in British Patent No. 1,251,590; or mechanically dispersing the compound, as described in Belgian Patent No. 852,138. Ultrasound can be employed to dissolve the compound prior to its incorporation in the photographic coating composition, as illustrated by Owen et al. U.S. Pat. No. 3,485,634 and Salmien U.S. Pat. No. 3,551,157. Alternatively, the compound can be dispersed directly in a hydrophilic colloid such as gelatin; or the compound can be loaded into latex and dispersed, as illustrated by Chen, Research Disclosure, Vol. 159, 1977, Item 15930.

Apparatus and procedures for introducing and blending bleach accelerator compounds are illustrated by Johnson et al U.S. Pat. Nos. 3,425,835; 3,570,818; 3,773,302 and 3,850,643; McCrossen et al U.S. Pat. No. 3,342,605, Collins et al U.S. Pat. No. 2,912,343 and Terwilliger et al U.S. Pat. Nos. 3,827,888 and 3,888,465.

U.S. Pat. No. 4,865,956 discloses a bleach accelerator silver salt having the structure:

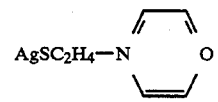

which, when incorporated in a photographic element, permits the element to be used in a multiplicity of bleach and bleach-fix compositions- The method used to incorporate the compound in the photographic element was catastrophic precipitation followed by ball milling as described in Swank et al., U.S. Pat. No. 4,006,025.

The above processes provide dispersions which may be difficult to reproduce. Further, dispersions prepared by these methods may contain a large amount of less active species of a bleach accelerator silver salt which can cause greatly reduced accelerating activity.

There is a need to produce a bleach accelerator silver salt compound with more consistent particle morphology and size, and hence, more reproducible bleach acceleration and photographic quality. There is further a need to produce a bleach accelerator silver salt dispersion which contains little or no inactive species. It is also desirable to produce it using a fast and efficient method.

SUMMARY OF THE INVENTION

This invention provides a process for preparing a bleach accelerator silver salt dispersion comprising precipitating a salt of a bleach accelerating compound and a silver salt wherein the vAg is maintained at a predetermined level. In one embodiment, the dispersion is precipitated in the presence of a surfactant.

This invention further provides a silver halide photographic element containing a bleach accelerating silver salt dispersion prepared by the above process. Additionally, this invention provides a silver halide photographic element containing a dispersion of grains of a bleach accelerating silver salt wherein the grains of the dispersion are substantially isomorphic.

It has been discovered that bleach accelerator silver salts can be quickly and efficiently produced by precipitation under controlled vAg, particularly in the presence of a non-ionic surfactant. With this process, the size and morphology of the precipitated microcrystals can be controlled and a morphologically pure dispersion can be produced. This provides more reproducible bleaching results. It has been further discovered that the activity of the bleach accelerator silver salt is affected by the level of vAg at which the bleach accelerator silver salt is precipitated.

BRIEF DESCRIPTION OF THE FIGURES

FIG. 1A is a scanning electron micrograph of a dispersion of needle shaped crystals of silver morpholino ethane thiol precipitated at a vAg of 190 mV.

FIG. 1B is a scanning electron micrograph of a dispersion of platelet shaped crystals of silver morpholino ethane thiol precipitated at a vAg of −80 mV.

DETAILED DESCRIPTION OF THE INVENTION

The bleach accelerator silver salts of this invention are bleach accelerator precursors which are substantially insoluble in an alkaline photographic developer solution but which have a relatively high solubility in an acidic bleach or bleach-fix solution. Preferred bleach accelerator silver salts are those which, when incorporated in a photographic element, have no adverse sensitometric effect on the photographic element and which are effective with a variety of bleach and bleach-fix compositions.

More preferred are those precursors which are silver salts of a solubilized, non-primary amino thiol, the precursor having a solubility of less than 1 g/l of silver ion, in a color developer solution comprising a pH of 10, a sulfite concentration of 4.25 g/l and a bromide concentration of 1.3 g/l, and having a solubility of greater than or equal to 1 g/l of silver ion in a bleach solution having a pH of 6 and a bromide ion concentration of 150 g/l, when held at 23° C. for five minutes in each of the solutions.

Preferred compounds are solubilized by one or more ether or thioether groups or by an additional nonprimary amino group. Especially preferred are those compounds solubilized with ether groups.

As used herein, solubility is defined as grams per liter of silver ion in solution when the test compound is treated as follows: 0.4 g of the test precursor is mixed with 10 ml of the developer or bleach shown below. The mixture is stirred for 30 seconds and held at 23° C. Five minutes after mixing a 20 μl aliquot is withdrawn, treated with cyanogeniodate to complex silver ion in solution and the silver ion present is measured by atomic absorption spectroscopy.

| Color Developer | |
| --- | --- |
| Water | 800 ml |
| Potassium carbonate (anh.) | 37.5 g |
| Sodium sulfite (dessic.) | 4.25 g |
| Potassium iodide | 1.2 mg |
| Sodium bromide | 1.3 g |
| Hydroxylamine sulfate | 2.0 g |
| Diaminopropanol tetraacetic acid | 2.5 g |
| 4-Amino-methyl-N-ethyl-N-β hydroxyethylaniline sulfate | 4.75 g |
| Potassium hydroxide (45%) | 0.65 ml |
| Water to total of | 1 liter |
| pH 10.0 | |
| Bleach | |
| Water | 600 ml |
| Ammonium bromide | 150 g |
| Ferric EDTA | 175 ml |
| Glacial acetic acid | 10.5 ml |
| Ptassium nitrate | 41.2 g |
| Water to total of | 2 liters |
| pH 6.0 | |

Representative precursor compounds useful in this invention are structurally shown below:

TABLE 1

1. 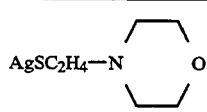

TABLE 1-continued

2. 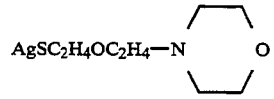

3. 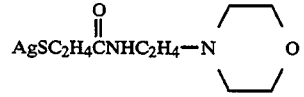

4. 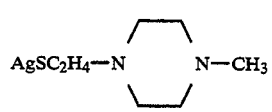

5. AgSC$_2$H$_4$OC$_2$H$_4$N(CH$_3$)
6. AgSC$_2$H$_4$N(C$_2$H$_4$OCH$_3$)

The use of these compounds is further described in Harder, U.S. Pat. No. 4,865,956, hereby incorporated by reference. Particularly preferred is silver morpholino ethane thiol (AgMET).

The dispersions of this invention are obtained by precipitating the bleach accelerator silver salt crystals while maintaining the vAg at a predetermined level. The size of the precipitated microcrystals are, in part, a function of the vAg, which is a measurement of silver ion activity in the following reaction:

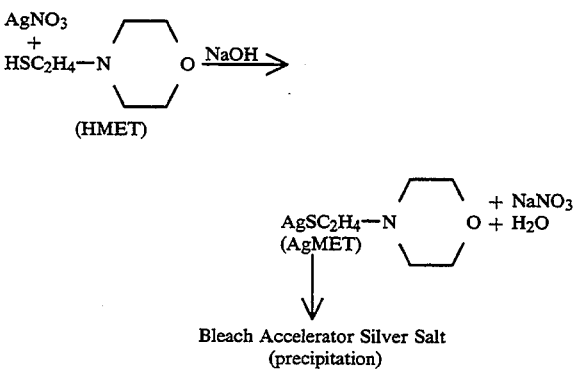

Bleach Accelerator Silver Salt (precipitation)

vAg herein is measured as mV of an Ag$_2$S electrode potential using an Ag/AgCl reference electrode.

Preferably, the precipitation is done in the presence of a small quantity of surfactant which helps reduce the particle size to the required range, possibly by restraining its growth and preventing flocculation.

A dispersion prepared at predetermined vAg will also be substantially isomorphic, that is, over 75%, and more preferably over 90%, of the grains in the dispersion will be of the same morphology, such as platelets of rectangular, hexagonal or parallelogram shape, needles or spheres. Because the morphology and size of the bleach accelerator silver salt crystals in a dispersion produced by the method of this invention are consistent and controllable, the amount of bleach acceleration provided by the bleach accelerator silver salt crystals is reproducible. The morphology and size may be controlled by adjusting the vAg, the type or amount of surfactant and the effectiveness of mixing. The morphology will also be dependent on the type of bleach accelerator silver salt. Dispersions containing bleach accelerator silver salts with different morphologies can be mixed into one emulsion layer.

It has further been discovered that the bleach acceleration activity of a bleach accelerator silver salt is a function of its morphology and size produced at various vAgs. Therefore, the amount of bleach acceleration achieved is dependent on the specific level of the vAg. In other words, the same bleach accelerator silver salt precipitated at two different predetermined vAgs will have different activities.

Generally, optimum bleach accelerating performance for the silver salts of the solubilized non-primary amino thiols described herein is obtained when the grains which are produced are platelet (having an aspect ratio greater than 5) or needle shaped as shown in FIGS. 1A and 1B.

The level of accelerating activity of a bleach accelerating silver salt precipitated at a specific vAg is retained through additional processing. Therefore, it has been found when such a dispersion is ball milled it has greater activity than a dispersion which has been catastrophically precipitated and ball milled. In one embodiment of this invention dispersions of bleach accelerator silver salts which have been precipitated at a predetermined level of vAg are then ball milled before incorporation into the emulsion.

The optimum vAg may be determined by doing a simple series of precipitations at varying vAgs and testing the activity of each. The morphology may be determined by scanning electron micrography at 1250X~20,000X magnification. Generally, the preferred vAg is maintained at a predetermined level within the range of from $-80$ mV to $+300$ mV, $+/-15$ mV with $+180$ mV to $+300$ mV $+/-15$ mV being more preferred.

The surfactants which are useful in the present invention are commercially available and comprise conventional water-soluble anionic and nonionic surface active agents. Various block copolymers of ethylene oxide and propylene oxide products have been found to be particularly advantageous. Examples of these are the propylene oxide, propylene glycol and ethylene oxide, propylene glycol copolymer products sold as Pluronic ®; Pluronic ® R; Tetronic ®; Tetronic ® R (BASF Corporation BASF Performance Chemicals, Parsippany, N.J. 07054 USA) and Dow Corning Surfactant 1430 and Antifoam B ® (Dow Corning Corporation, Midland, Mich. 48686 USA).

The bleach accelerator silver salt dispersions of the present invention may be prepared by the following double jet precipitation method. An aqueous solution of a silver salt such as $AgNO_3$, $Na_3Ag(S_2O_3)_2$ or $NH_4AgS_2O_3$, with $AgNO_3$ being preferred, is prepared at a concentration of 2.0 moles/liter to 0.001 mole/liter. Separately prepared is an aqueous solution of a bleach accelerating compound in the salt form at a concentration of 2.0 moles/liter to 0.001 mole/liter. The two solutions are added to a reaction vessel as two separate streams which meet at a mixing point within the reactor. Double jet precipitation of silver halide grains is a method well known in the art and is described in *The Theory of the Photographic Process*, Fourth Edition, by T. H. James, MacMillan Publishing Co., Inc., New York, N.Y. 10022, 1977, at page 88. The vAg of the reaction is maintained at a level which is predetermined as described above. Generally the aqueous silver salt stream is pumped at a constant rate while the aqueous bleach accelerator salt stream is pumped at a varying rate to maintain the predetermined constant vAg value.

The bleach accelerator silver salt may also be prepared by a single jet precipitation method which involves the neutralization of a soluble acidic complex, an example of which is shown below, to form an insoluble precipitate.

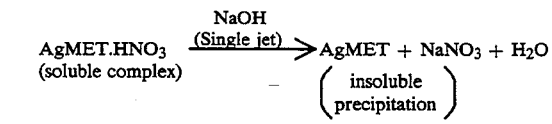

The acidic complex $AgMET-HNO_3$ is formed by mixing $AgNO_3$ and morpholino ethane thiol (HMET) at room temperature. Different vAg levels may be maintained by mixing $AgNO_3$ and HMET at various ratios. The above single jet precipitation ends when the pH is 5.14 or above. vAg at the precipitation pH depends on the initial ($AgNO_3$/HMET) ratio.

Preferably, a surfactant is mixed with distilled water at a concentration level of 0.01 to 12.0, preferably 0.1 to 1.2 percent by weight and charged into the reaction vessel during the precipitation process. The precipitated bleach accelerator silver salt may be washed and separated from the soluble salt by ultrafiltration (UF) or by sedimentation. Gelatin is then added to the washed bleach accelerator silver salt to form a uniform and stable bleach accelerator silver salt dispersion ready for incorporation into a silver-halide photographic element.

The photographic elements useful with this invention can be single-color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single-segmented layer, e.g., as by the use of microvessels as described in Whitmore, U.S. Pat. No. 4,362,806, issued Dec. 7, 1982. The element can contain additional layers such as filter layers, interlayers, overcoat layers, subbing layers, and the like.

One or more bleach accelerator silver salts of the invention can be located in the photographic element at any convenient location capable of permitting diffusion of the released active fragment to a silver containing emulsion layer during bleaching. Additionally, more than one emulsion within a photographic element may contain bleach accelerator silver salt compounds. The compound can be incorporated directly in the silver halide emulsion layer from which silver is to be leached. It can also be located in any other bleach solution permeable layer of the photographic element on either side of the support, particularly any layer adjacent to the emulsion layer from which silver is to be bleached. A preferred location is in the bottom layer near the base of a multiple layer product; for example the bleaching of silver from the usually lowermost red-sensitized emulsion layer in a color photographic element can be enhanced by incorporation of the bleach accelerator silver salt in an underlaying antihalation layer.

Preferably, the bleach accelerator silver salts are incorporated in a photographic element at levels in the range of from 0.01 to 10 g/m$^2$, with levels of from 0.05 to 0.15 g/m$^2$ being optimum for ordinarily encountered silver levels. For photographic elements having elevated silver levels, still higher levels of the compounds may be desirable.

The bleaches which may be utilized with this invention are those generally known in the art. A variety of bleach compositions have been employed with silver halide materials. These include those based on, e.g., ferricyanide, dichromate, permanganate, chloride, quinone, as well as aminocarboxylic acid and persulfate oxidizing agents. Typical compositions containing such oxidizing agents for the bleaching of photographic image silver are referred to or described in U.S. Pat. Nos. 3,512,979; 3,615,513; 3,647,469; 3,689,272; 3,706,561; 3,716,362; 9,749,572; 3,772,020; 3,893,858; 4,163,669; 4,292,401; 4,293,639; 4,301,236; 4,322,493; 4,448,878; 4,458,010; 4,481,290; 4,524,129; 4,546,070; and 4,596,764.

Other descriptions of the composition and use of photographic silver bleaches are found on pages 124 and 125 of Neblette's *Handbook of Photography and Reprography, Materials, Processes and Systems*, Seventh Edition, Van Nostrand Reinhold Company; and on pages 447 to 450 of *The Theory of the Photographic Process*, Fourth Edition, MacMillan Publishing Co., Inc., New York, London.

Preferred bleaches are aminopolycarboxylic acid, ferric complex salt bleaches and persulfate bleaches. Examples of useful aminopolycarboxylic acid ferric complexes include: N-(2-Acetamido)iminodiacetic acid ferric complex salt, Methyliminodiacetic acid ferric complex salt, Iminodiacetic acid ferric complex salt, 1,4-butylenediaminetetraacetic acid ferric complex salt, diethylenethioetherdiaminetetraacetic acid ferric complex salt, glycoletherdiaminetetraacetic acid ferric complex salt, 1,3-propylenediaminetetraacetic acid ferric complex salt and ethylenediaminetetraacetic acid ferric salt. Most preferred bleaches are the persulfate bleaches.

In the following discussion of suitable materials for use in the emulsions and elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, the disclosures of which are incorporated herein by reference. This publication will be identified hereafter by the term "Research Disclosure".

The silver halide emulsions employed in the elements of this invention can be either negative-working or positive-working. Examples of suitable emulsions and their preparation are described in Research Disclosure Sections I and II and the publications cited therein. Some of the suitable vehicles for the emulsion layers and other layers of elements of this invention are described in Research Disclosure Section IX and the publications cited therein.

The silver halide emulsions can be chemically and spectrally sensitized in a variety of ways, examples of which are described in Sections III and IV of the Research Disclosure. The elements of the invention can include various couplers including, but not limited to, those described in Research Disclosure Section VII, paragraphs D, E, F, and G, and the publications cited therein. These couplers can be incorporated in the elements and emulsions as described in Research Disclosure Section VII, paragraph C, and the publications cited therein.

The photographic elements of this invention or individual layers thereof can contain among other things brighteners (examples in Research Disclosure Section V), antifoggants and stabilizers (examples in Research Disclosure Section VI), antistain agents and image dye stabilizers (examples in Research Disclosure Section VII, paragraphs I and J), light absorbing and scattering materials (examples in Research Disclosure Section VIII), hardeners (examples in Research Disclosure Section X), plasticizers and lubricants (examples in Research Disclosure Section XII), antistatic agents (examples in Research Disclosure Section XIII), matting agents (examples in Research Disclosure Section XVI), and development modifiers (examples in Research Disclosure Section XXI).

The photographic elements can be coated on a variety of supports including, but not limited to, those described in Research Disclosure Section XVII and the references described therein.

Photographic elements can be exposed to actinic radiation, typically in the visible region of the spectrum, to form a latent image as described in Research Disclosure Section XVIII and then processed to form a visible dye image, examples of which are described in Research Disclosure Section XIX. Processing to form a visible dye image includes the step of contacting the element with a color-developing agent to reduce developable silver halide and oxidize the color-developing agent. Oxidized color-developing agent, in turn, reacts with the coupler to yield a dye.

The color-developing solutions typically contain a primary aromatic amino color-developing agent. These color-developing agents are well known and widely used in variety of color photographic processes. They include aminophenols and p-phenylenediamines.

In addition to the primary aromatic amino color-developing agent, color-developing solutions typically contain a variety of other agents, such as alkalies to control pH, bromides, iodides, benzyl alcohol, antioxidants, antifoggants, solubilizing agents, brightening agents, and so forth.

Photographic color-developing compositions are employed in the form of aqueous alkaline-working solutions, having a pH of above 7, and most typically in the range of from about 9 to about 13. To provide the necessary pH, they contain one or more of the well known and widely used pH buffering agents, such as the alkali metal carbonates or phosphates. Potassium carbonate is especially useful as a pH buffering agent for color-developing compositions.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching and fixing to remove silver and silver halide, washing, and drying.

Fixing agents include compounds which react with silver halide to form a water-soluble complex salt, e.g., thiosulfates such as potassium thiosulfate, sodium thiosulfate and ammonium thiosulfate; thiocyanates such as potassium thiocyanate, sodium thiocyanate and ammonium thiocyanate; thioureas; thioethers, and halides such as iodides.

The fixer may contain one or more pH buffers comprising various acids and salts such as boric acid, borax, sodium hydroxide, potassium hydroxide, sodium carbonate, potassium carbonate, sodium bicarbonate, potassium bicarbonate, acetic acid, sodium acetate and ammonium hydroxide, as well as fixing agent. Also, it is possible to add, as appropriate, substances known to be usually added to the fixer, such as pH buffers, e.g., borates, oxalates, acetates, carbonates, phosphates, alkylamines, and polyethyleneoxides.

The above fixing agents are normally used at over 0.1 mol per 1 processing solution; from the viewpoint of the desired effect of the invention, it is preferable to use these agents in the range of from 0.6 to 4 mols, more preferably 0.9 to 3.0 mols, still more preferably 1.1 to 2.0 mols.

Typically, a separate pH lowering solution, referred to as a stop bath, is employed to terminate development prior to bleaching. A stabilizer bath is commonly employed for final washing and hardening of the bleached and fixed photographic element prior to drying. Conventional techniques for processing are illustrated by Research Disclosure, Paragraph XIX.

The following examples are intended to illustrate, without limiting, this invention.

EXAMPLE 1

Preparation of Dispersion A

| Solution A: | |
|---|---|
| BASF Surfactant Pluronic ® R 25R8 | 1.0 g |
| Water | 399.0 g |
| Solution B: | |
| Morpholino ethane thiol | 29.4 g |
| 2.5N NaOH | 80.0 g |
| Water | 1890.6 g |
| Solution C: | |
| AgNO$_3$ | 13.6 g |
| Water | 1000.0 g |

Solution A was charged into a 1000 mL kettle. While Solution A was under vigorous stirring, Solution B and Solution C were pumped separately into the kettle, and the two solutions met each other at the mixing point under the liquid surface, near the bottom of the kettle. Solution C was pumped into the kettle at 20 mL/min, and Solution B was pumped into the kettle at a rate to maintain the vAg, measured near the mixing point, at −60.0 mV. The following precipitation reaction occurs within the reactor:

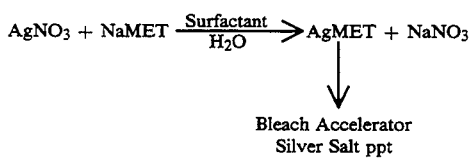

Bleach Accelerator
Silver Salt ppt

After 10 minutes running, both pumps were shut down; the resulting milky white solution, about 800 mL, was sent to a portable ultrafiltration unit (Model CH2, Ultrafiltration System, Amicon Division, W. G. Grace & Co., Danvets, Mass., 01923) for washing and removal of the water-soluble NaNO$_3$ salts. The final volume of the washed water-insoluble AgMET slurry was concentrated down to about 300 mL. This 100 mL slurry was transferred to a constant temperature bath set at 41° C., and 5.0 g gelatin was; added to this slurry and stirred for 30 minutes to form a uniform dispersion of AgMET. The solid AgMET content of this dispersion was measured at about 3.8% by weight. The dispersion (Dispersion A) was ready for incorporation into a silver halide photographic element.

Preparation of Dispersion B

A dispersion of AgMET (Dispersion B) was prepared in the same manner as Dispersion A, except that the vAg set during the precipitation was maintained at 0 mV.

Preparation of Dispersions C Through J

Dispersions C through J were prepared in the same manner as Dispersion A, except that the vAg was set at different values as summarized in Table I below:

TABLE I

| Dispersion ID And Its Making vAg (mV) | | | | | | | | | |
|---|---|---|---|---|---|---|---|---|---|
| Dispersion ID | A | B | C | D | E | F | G | H | I | J |
| Making vAg (mV) | −60 | 0 | 60 | 80 | 120 | 180 | 240 | 300 | 360 | 420 |

These dispersions were incorporated in the antihalation layer below the cyan coupler layer of a photosensitive film unit of the following structure:
5.84 (g/m$^2$) gelatin + .248 (g/m$^2$) hardener
0.950 (g/m$^2$) Fast AgBrI T-grain type emulsion
.130 (g/m$^2$) cyan coupler and 1.7 (g/m$^2$) gelatin
2.0 (g/m$^2$) slow AgBrI T-grain type emulsion
.650 (g/m$^2$) cyan coupler + 2.63 (g/m$^2$) gelatin
.200 (g/m$^2$) gray silver + .038 (g/m$^2$) Ag.MET
2.27 (g/m$^2$) gelatin
Clear Support The test and control film units were identically exposed in an intensity scale sensitometer and processed in the process described in Table II. The resulting retained silver, which is the measurement of bleaching activities of the incorporated AgMET dispersions, are listed in Table III as % retained silver at bleaching times of 30 seconds and 120 seconds. Lower retained silver means higher bleaching activity of the bleach accelerator silver salt.

TABLE II

| Process And Composition Of Processing Solutions | | |
|---|---|---|
| Process | Time | Temperature (°F.) |
| p-phenylenediamine Developer | 3'15" | 100 |
| Stop | 1'00" | 95 |
| Water Wash | 1'00" | 98 |
| *Bleach | 2'00" | 98 |
| Water Wash | 3'00" | 96 |
| Amino Thiosulfate Fix | 4'00" | 100 |
| Water Wash | 3'00" | 96 |
| Formaldehyde Stabilizer | 1'00" | 100 |
| *Bleach formulation | | |
| Water | 800 ml | |
| Gelatin | 0.5 g | |
| Sodium Persulfate | 33.0 g | |
| Sodium Chloride | 15.0 g | |
| Sodium Dihydrogen Phosphate | 9.0 g | |
| Water To Make | 1.0 liter | |

TABLE III

Bleaching Activity And AgMET Precipitation vAg (mV)

| Dispersion ID | Precipitation vAg (mV) | Amt. In Film (g/m²) | % Retained Silver* After Bleaching Time Of | |
|---|---|---|---|---|
| | | | 30 sec | 120 sec |
| Control | — | 0 | 97.3 | 95.1 |
| A | −60 | 0.138 | 1.7 | 1.3 |
| B | 0 | 0.138 | 17.0 | 5.9 |
| C | 60 | 0.138 | 3.2 | 0.5 |
| D | 80 | 0.138 | 18.7 | 3.4 |
| E | 120 | 0.138 | 2.5 | 2.2 |
| F | 180 | 0.138 | 2.6 | 2.2 |
| G | 240 | 0.138 | 5.5 | 3.6 |
| H | 300 | 0.138 | 10.8 | 2.5 |
| I | 360 | 0.138 | 90.5 | 81.3 |
| J | 420 | 0.138 | 88.4 | 83.3 |

*% Retained Silver = $\dfrac{\text{Silver in the film after processing by Table II processing}}{\text{Silver in the film after developer process of Table II}}$ Silver measured by x-ray fluorescence.

From Table III, it can be seen that Dispersions A through H have significantly higher bleaching activities than Dispersions I and J. Further, Dispersions A through H, made according to the present invention, show excellent bleaching acceleration activity compared to the control without any bleaching accelerator. It also illustrated that control of precipitation vAg is necessary to obtain dispersions of high bleaching acceleration activity and better processed color film of lower retained silver.

EXAMPLE 2

Preparation of Dispersions K, L and O

Three more dispersions of AgMET (Dispersions K, L and O) were prepared in the same manner as dispersion A of Example I except that the vAg during the precipitation was set at different values as shown in Table IV. The morphologies of the microcrystalline AgMET grains precipitated at different vAg are also listed in Table IV.

Preparation of Dispersion M

| Solution D: | |
|---|---|
| Morpholino ethane thiol | 3.09 g |
| AgNO₃ | 2.97 g |
| BASF Pluronic ® R 25R8 | 1.75 g |
| Water | 343.94 g |
| Solution E: | |
| NaOH | 20.00 g |
| Water | 500.00 g |

This dispersion was prepared using a single jet precipitation process.

Solution D was charged into a 1,000 ml kettle. While Solution D was under vigorous stirring, Solution E was pumped into the kettle at 10 ml/min under the liquid surface, near the bottom of the kettle. The following precipitation reaction occurs within the reactor:

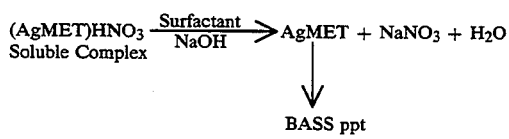

After 9 minutes running, the Solution E pump was shut down when the pH of the liquid in the kettle reached 5.14 and vAg was −60 mV. The resulting milky white liquid, about 450 ml, was sent to ultrafiltration washing and was made into a 5% gelatin dispersion the same way as Dispersion A of Example I. Dispersion M shown in SEM at 1250X contained ellipse platelets of fairly uniform size and shape.

Preparation of Dispersions N, P, O and R

Dispersions N, P, Q and R were prepared in the same manner as Dispersion M, except the vAgs monitored during the precipitation were at different values as summarized in Table IV. The different morphologies of the precipitated microcrystalline materials obtained at the different vAg are also listed in Table IV.

In the low vAg range (vAg<180 mv or pAg>5.8), the precipitated grains were substantially thin platelet or tabular type with an aspect ratio around 10. Several isomorphic forms of this type of thin platelets were generated, including parallelogram (−150 mv precipitated), hexagon (−80 mv precipitated), ellipse (−60 mv precipitated), and rectangular (+30 mv precipitated) shapes.

In the middle vAg range (180<vAg<320 mv), the precipitated crystallines were mostly needle or aggregates of needles. Separated long needles were precipitated around 190 mv.

In the high vAg range (vAg>320 mv), three dimensional spherical particles of sub-micron sizes were precipitated. These spherical particles had very little bleaching acceleration capability, although they formed very stable dispersions due to their sub-micron sizes.

TABLE IV

Morphologies Of AgMET, Precipitated At Various vAg

| Dispersion ID | Fig. No. | Precipitation vAg | Morphology |
|---|---|---|---|
| K | 1 | −150 mv | Parallelogram Platelet |
| L | 2 | −80 mv | Hexagon Platelet |
| M | 3 | −60 mv | Ellipse Platelet |
| N | 4 | 30 mv | Rectangular Platelet |
| O | 5 | 190 mv | Needle |
| P | 6 | 420 mv | Sphere |
| Q | 7 | 450 mv | Sphere |
| R | 8 | 480 mv | Sphere |

EXAMPLE 3

Preparation of Dispersion S

Slurry F:

| Needle shaped AgMET crystals(precipitated at 180 mV similar to Dispersion O described in Example 2) | 100 g |
|---|---|
| OLIN 10 G (olonylphenoxypolyglycerol) ® (Olin Corp. 120 Long Ridge Road Stamford, CT 06904) | 9 g |
| Gelatin | 10 g |
| Distilled water | 881 g |

The above Slurry F, about 1,000 grams, was circulated through a media mill machine "Dyno Mill Type KDL" (Dyno Mill, manufactured by Willy A. Bachofen AG Maschinenfabrik, H-4005 Basel, Utengasse 15-17, Schweiz). The mill was filled with 0.5 mm diameter Zr-Si beads (used as milling media). The slurry was mixed with the beads by the rotating screw of the mill rotated at 2000 revolutions per minute. The slurry was circulated through the mill for 2 hours while the temperature of the milling media was maintained at 40° C.

At the end of 2 hours of milling, the milled Slurry F went through a screen which separated the beads and the milled slurry. SEM showed an average milled AgMET size of 0.6 um. In a separate constant temperature bath the above milled slurry was heated to 40° C, and an additional 40 grams of gelatin were added and stirred for 30 minutes. This was Dispersion S which contained approximately 10% milled solid AgMET and 5% gelatin. Dispersion S was incorporated into the antihalation layer below the cyan coupler layer of a photosensitive film unit as described in Example 1. After processing as described in Example 1 the following bleaching was noted.

| Dispersion ID | Precipitation vAg (mV) | Amt. In Film (g/m²) | % Retained Silver* After Bleaching Time Of | |
|---|---|---|---|---|
| | | | 30 sec | 120 sec |
| S | 180 | 0.138 | 18.7 | 3.4 |

*% Retained Silver = $\frac{\text{Silver in the film after processing by Table II processing}}{\text{Silver in the film after developer process of Table II}}$ Silver measured by x-ray fluorescence.

The invention has been described in detail with particular reference to preferred embodiments thereof, but it will be understood that variations and modifications can be effected within the spirit and scope of the invention.

What is claimed is:

1. A process for preparing a bleach accelerator silver salt dispersion comprising precipitating a salt of a bleach accelerating compound and a silver salt wherein the vAg is maintained at a predetermined level and wherein the precipitated bleach accelerator silver salt is additionally processed to reduce the size of the silver salt grains.

2. The process of claim 1 wherein the vAg is maintained at a level within the range of from −80 mV to +300mV.

3. The process of claim 2 wherein the vAg is maintained at a level in the range from +180 mV to +300mV.

4. The process of claim 1 wherein the bleach accelerating compound is a non-primary amino thiol.

5. The process of claim 1 wherein the bleach accelerating compound is morpholino ethane thiol.

6. The process of claim 1 wherein the dispersion is precipitated in the presence of a surfactant.

7. The process of claim 6 wherein the surfactant is a block copolymer of ethylene oxide and propylene oxide.

8. The process of claim 1 wherein the precipitated bleach accelerator silver salt is filtered to eliminate the water soluble salts in the precipitated dispersion.

9. The process of claim 1 wherein the salt of the bleach accelerating compound and the silver salt are precipitated by double jet precipitation.

10. The process of claim 1 wherein the precipitated bleach accelerator silver salt is additionally processed by ball milling.

11. The process of claim 1 wherein the salt of the bleach accelerating compound and the silver salt are precipitated by double jet precipitation in the presence of a surfactant and then filtered to eliminate the water soluble salts in the precipitated dispersion.

12. The process of claim 11 wherein the surfactant is a block copolymer of ethylene oxide and propylene oxide.

13. A process for preparing a bleach accelerator silver salt dispersion comprising:
   precipitating a salt of a non-primary amine thiol bleach accelerating compound and a silver salt by double jet precipitation in the presence of a surfactant;
   wherein the vAg is maintained from −80 mV to +300 mV and wherein the precipitated bleach accelerator silver salt is additionally processed to reduce the size of the silver salt grains.

14. The process of claim 13 wherein the vAg is from +180 mV to +300 mV.

15. The process of claim 13 wherein the bleach accelerating compound is morpholino ethane thiol.

16. The process of claim 13 wherein the surfactant is a block copolymer of ethylene oxide and propylene oxide.

17. The process of claim 13 wherein the precipitated bleaching accelerator silver salt is filtered to eliminate the water soluble salts in the precipitated dispersion.

18. The process of claim 13 wherein the precipitated bleach accelerator silver salt is additionally processed by ball milling.

19. A silver halide photographic element containing a bleach accelerator silver salt dispersion prepared by any one of the processes of claims 1 through 18.

20. A silver halide photographic element containing a dispersion of grains of a bleach accelerator silver salt wherein the grains are substantially isomorphic.

21. The silver halide photographic element of claim 20 wherein the bleach accelerating compound is a non-primary amine thiol.

22. The silver halide photographic element of claim 21 wherein the bleach accelerating compound is morpholino ethane thiol.

23. The silver halide photographic element of claim 20 wherein the grains are needle shaped or platelet shaped.

* * * * *